United States Patent [19]

Botta et al.

[11] Patent Number: 4,960,943

[45] Date of Patent: Oct. 2, 1990

[54] PROCESS FOR THE PREPARATION OF PHENYLKETONES ETHERIFIED IN THE 4-POSITION

[75] Inventors: Artur Botta; Hans-Josef Buysch, both of Krefeld; Lothar Puppe, Burscheid; Dieter Arlt, Cologne, all of Fed. Rep. of Germany

[73] Assignee: Bayer Aktiengesellschaft, Leverkusen, Fed. Rep. of Germany

[21] Appl. No.: 318,088

[22] Filed: Mar. 2, 1989

[30] Foreign Application Priority Data

Mar. 19, 1988 [DE] Fed. Rep. of Germany ....... 3809260

[51] Int. Cl.$^5$ .............................................. C07C 45/46
[52] U.S. Cl. ..................................... 568/319; 568/322
[58] Field of Search ....................... 568/319, 322, 373

[56] References Cited

U.S. PATENT DOCUMENTS 4,304,941 12/1981 Lee et al. ............................ 568/322
4,652,683 3/1987 Nicolau et al. ..................... 568/319
4,694,111 9/1987 Gupta ................................. 568/322
4,714,781 12/1987 Gupta ................................. 568/319

FOREIGN PATENT DOCUMENTS 0279322 8/1988 European Pat. Off. ............ 568/322

OTHER PUBLICATIONS

Fujiwa et al., Chem. Abst., vol. 108, #221290v (1988).

Primary Examiner—James H. Reamer
Attorney, Agent, or Firm—Sprung Horn Kramer & Woods

[57] ABSTRACT

Phenylketones etherified in the 4-position can be prepared by reaction of aromatic ethers which have a free 4-position with acylating agents, the acylation being carried out in the presence of zeolite catalysts having pore sizes of at least 5 Å.

18 Claims, No Drawings

PROCESS FOR THE PREPARATION OF PHENYLKETONES ETHERIFIED IN THE 4-POSITION

BACKGROUND OF THE INVENTION

The invention relates to a process for the preparation of phenylketones etherified in the 4-position by reaction of aromatic ethers which have a free 4-position with conventional acylating agents on medium-pored or wide-pored zeolites having a pore size of at least 5 Å.

Aromatic ketones containing ether groups, for example 4-methoxyacetophenone or 4-methoxypropiophenone, are of great interest in the fragrance industry or as intermediates for other syntheses. The conventional method for the preparation of aromatic ketones is the homogeneous Friedel-Crafts acylation of aromatic hydrocarbons with carboxylic acid derivatives; in this form, acylation is also carried out in industry. For this purpose, at least stoichiometric, in most cases, however, excess amounts of the catalyst are, as is known, required, such as Lewis acids ($AlCl_3$, $FeCl_3$, $BF_3$, $ZnCl_2$, $TiCl_4$) or proton acids (polyphosphoric acid, HF). Reference is made, for example, to the monograph by G. A. Olah, "Friedel-Crafts and related reactions", Wiley-Interscience, New York, Vol. I–IV (1963–1964) or to DE-OS (German Published Specification) 3,519,009. The problematical nature of Friedel-Craft catalysis when carried out in industry, that is, high costs through increased corrosion and also significant expenditure in handling, removal and disposal of the ultimately consumed catalyst, is sufficiently known.

In the special case where aromatics containing ether groups are used, moreover cleavage of the ether or rearrangement into the ring of the hydrocarbon radical bound to the ether oxygen must be expected in addition.

SUMMARY OF THE INVENTION

A process for the preparation of phenylketones etherified in the 4-position of the formula

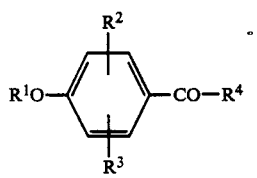
(I)

by reaction of aromatic ethers of the formula

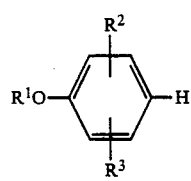
(II)

with acylating agents of the formula $$X\text{—}CO\text{—}R^4 \qquad (III)$$

in which formulae $R^1$ stands for $C_1$–$C_{12}$-alkyl, $C_2$–$C_{12}$-alkenyl, $C_3$–$C_7$-cycloalkyl or $C_6$–$C_{10}$-aryl, $R^2$ and $R^3$ independently of one another denote hydrogen, fluorine, chlorine, bromine, $C_1$–$C_4$-alkyl or $C_3$–$C_7$-cycloalkyl, $R^4$ denotes $C_1$–$C_{16}$-alkyl, $C_2$–$C_{16}$-alkenyl, $C_3$–$C_7$-cycloalkyl, $C_7$–$C_{12}$-aralkyl, $C_8$–$C_{12}$-aralkenyl or $C_6$–$C_{12}$-aryl and X stands for chlorine, bromine, $OCOR^4$, $C_1$–$C_2$-alkoxy, hydroxyl, amino, NH-$C_1$–$C_4$-alkyl or N($C_1$–$C_4$-alkyl)$_2$ has now been found, which is characterized in that the reaction is carried out in the presence of zeolite catalysts of the formula $$M_{m/z}[mMe^1O_2 \cdot nMe^2O_2] \cdot q\ H_2O \qquad (IV)$$

in which

M is an exchangeable cation, z is the valence of the cation, $Me^1$ and $Me^2$ represent the elements of the anionic skeleton, n/m denotes the ratio of the elementals and adopts values of 1–3000, preferably 1–2000, and q denotes the amount of the water adsorbed, the zeolites having pore sizes of at least 5 Å.

DETAILED DESCRIPTION OF THE INVENTION $R^1$ can denote $C_1$–$C_{12}$-alkyl, preferably $C_1$–$C_4$-alkyl, particularly preferably $C_1$–$C_2$-alkyl, very particularly preferably methyl. Apart from methyl, examples are ethyl, propyl, isopropyl, butyl, isobutyl, the isomeric amyls, hexyls, octyls, decyls, dodecyls. Furthermore, $R^1$ can denote $C_2$–$C_{12}$-alkenyl, preferably $C_2$–$C_4$-alkenyl such as vinyl, propenyl, butenyl, the isomeric amylenes, hexenes, octenes, decenes, dodecenes. Furthermore, $R^1$ can denote $C_6$–$C_{10}$-aryl such as phenyl or naphthyl, preferably phenyl. Furthermore, $R^1$ can denote $C_3$–$C_7$-cycloalkyl such as cyclopropyl, cyclobutyl, cyclopentyl, methylcyclopentyl, cyclohexyl, methylcyclohexyl or cycloheptyl. $R^2$ and $R^3$ independently of one another can denote $C_1$–$C_4$-alkyl, preferably $C_1$–$C_2$-alkyl, particularly preferably methyl. Furthermore, $R^2$ and $R^3$ independently of one another can denote $C_3$–$C_7$-cycloalkyl to the above extent, preferably cyclopropyl, cyclopentyl and cyclohexyl. $R^4$ can denote $C_1$–$C_{16}$-alkyl, preferably $C_1$–$C_{12}$-alkyl, particularly preferably $C_1$–$C_4$-alkyl, for example of the abovementioned type. Furthermore, $R^4$ can denote $C_2$–$C_{16}$-alkenyl, preferably $C_2$–$C_4$-alkenyl, for example of the abovementioned type. Furthermore, $R^4$ can denote $C_3$–$C_7$-cycloalkyl, for example of the abovementioned type. Furthermore, $R^4$ can denote $C_7$–$C_{12}$-aralkyl, preferably $C_7$–$C_9$-aralkyl, for example benzyl, 1-phenylethyl, 2-phenylethyl, naphthylmethyl, naphthylethyl; benzyl is particularly preferred. Furthermore, $R^4$ can denote $C_6$–$C_{12}$-aryl such as phenyl, naphthyl or biphenyl, preferably phenyl. Furthermore, $R^4$ can denote $C_8$–$C_{12}$-aralkenyl, preferably styryl.

The radicals mentioned can themselves be substituted by fluorine, chlorine, bromine, $C_1$–$C_4$-alkyl, $C_1$–$C_4$-alkoxy or $C_1$–$C_4$-alkylthio. Furthermore, $R^4$ can be substituted by a second carboxyl group or a functional derivative thereof.

Suitable acylating agents are the acids derived from formula (III), halides thereof, esters thereof, anhydrides thereof, substituted or unsubstituted amides thereof; suitable examples are in particular the anhydrides and the chlorides.

A representative example of the reaction according to the invention is the reaction of anisole with acetic anhydride, which can be illustrated by the following formula scheme:

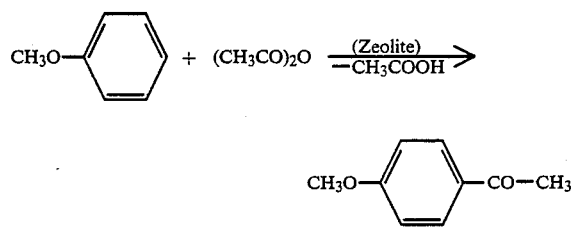

The disadvantages mentioned of the known processes are avoided by the process according to the invention. It is true that it is already known to react lower-alkyl-substituted benzenes without hydroxyl groups in the presence of zeolites with carboxylic acids or derivatives of carboxylic acids, preferably in the gas phase, to give aromatic ketones. In this reaction, using acetic acid on pentasils (EP 239,383) or on zeolite SE-Y (DE-OS (German Published Specification) 2,616,583), conversions in the order of no more than 5% are obtained. According to FR 2,592,039 or J. Org. Chem. 51 (1986), 2128–2130, higher conversions are only obtained with carboxylic acids having longer chains. On the other hand, US 4,652,683, US 4,668,826 and EP 227,331 report the acylation of phenol with carboxylic acids in the gas phase on silicalite or H-ZSM 5 to form, preferably, 2-hydroxyphenyl lower-alkyl ketones; however, in this reaction some by-products such as phenyl acetate or secondary products, for example heterocycles such as 2-methylchromone and 4-methylcoumarin occur. Mixtures of this type consisting of esters, ketones and heterocycles are also the result of the reaction of phenols with acetic anhydride in the gas phase, for example of mordenite (Kin. Katal. 23 (1982/2), 417–420; cited according to C.A. 97, 72 012 f).

In view of the prior art mentioned, it could not be expected that in the process according to the invention, even in the case of short-chain carboxylic acid derivatives such as acetic anhydride, it is possible to obtain excellent conversions of 75% or more and that furthermore 4-alkoxyphenylketones instead of the 2-alkoxy isomers are obtained at a high selectivity of 98–100% and that finally under the reaction conditions the alkoxyaromatics do not undergo cleavage of the ether and/or rearrangement reactions to give phenols or cresols on the zeolites, if these are used in their acidic form.

Examples of aromatic ethers for the process according to the invention are as follows: anisole, o- and m-methylanisole, o- and m-chloro- or bromoanisole, o-ethylanisole, phenetol, o- and m-methylphenetol, m-chlorophenetol, propoxy-, butoxy-, isobutoxy-, amyloxy-, octyloxy-, decyloxy-, lauryloxy-, cyclohexyloxy-, benzyloxy-, hexenyloxybenzene, -3-chlorobenzene, -3-methylbenzene, -2-ethylbenzene, diphenyl ether, 2-chlorodiphenyl ether, -3-methyldiphenyl ether.

Examples of acylating agents for the process according to the invention are as follows: acetic acid, acetyl chloride, acetyl bromide, acetic anhydride, methyl acetate, acetamide, propionic acid, propionyl chloride, propionic anhydride, butyric acid, butyryl chloride, butyric anhydride, isobutyric acid, isobutyryl chloride, isobutyric anhydride, pivaloyl chloride, pivalic anhydride, valeric acid, valeryl chloride, valeric anhydride, caproyl chloride, isooctanoyl chloride, lauroyl chloride, chloroacetyl chloride, dichloroacetyl chloride, dichlorofluoroacetyl chloride, chlorobutyryl chloride, methoxyacetic anhydride, butylmercaptoacetic acid, butylmercaptoacetyl chloride, acrylic acid, methacryloyl chloride, cyclopropanecarbonyl chloride, cyclohexanecarbonyl chloride, phenylacetyl chloride, phenylacetic anhydride, dihydrocinnamoyl chloride, cinnamoyl chloride, benzoyl chloride, benzoic anhydride, methyl benzoate, o-, m-, p-fluoro-, -chloro-, -bromo- and -iodobenzoyl chloride, o-, m-, p-methyl-, -isopropyl-, -methoxybenzoyl chloride, dichloro-, dimethyl-, methoxymethylbenzoyl chloride, chloromethylbenzoyl chloride, malonic anhydride, dimethylmalonyl dichloride, succinic anhydride, glutaric anhydride, phthalic anhydride, phthaloyl dichloride, tetrahydrophthalic anhydride.

The amount of acylating agent used can be varied within wide limits in the process according to the invention. In general the acylating agent is used in a stoichiometric ratio with respect to the aromatic ether. However, it can also be advantageous to use one component in excess, for example 0.2–5 mole, preferably 0.5–2 mole, of the ether, relative to the acylating agent.

The process according to the invention is carried out in the presence of zeolite catalysts of the formula (IV). As for their basic structure, zeolites are crystalline alumosilicates made up of a network of $SiO_4$ and $AlO_4$ tetrahedra. The individual tetrahedra are connected to one another via the edges by means of oxygen bridges and form a three-dimensional network uniformly permeated by channels and void spaces. The individual zeolite structures differ in the arrangement and size of the channels and void spaces and also in their composition. Exchangeable cations are incorporated to balance the negative charge of the lattice. Zeolites which can be used according to the invention belong to the formula (IV). In this formula, q $H_2O$ represents an absorbed water phase which can be removed reversibly without destroying the structure of the framework. In (IV) $Me^1$ is in general aluminum which, however, can be partly replaced by other elements, for example, such as B, Ga, In, Fe, Cr, V, As, Sb or Be.

Furthermore, $Me^2$ in (IV) is mainly silicone, which can, however, be replaced by other tetravalent elements such as, for example Ge, Ti, Zr or Hf.

An extensive description of zeolites is given, for example, in the monograph by D. W. Breck "Zeolite Molecular Sieves, Structure, Chemistry and Use", J. Wiley and Sons, New York, 1974.

Preferably, zeolites of the following structure types can be used in the process according to the invention: faujasite, L, mordenite, mazzite, offretite, gmelinite, cancrinite, ZSM 12, ZSM 25, zeolite β, ferrierite, ZSM 5, ZSM 11, heulandite, ZSM 22, ZSM 23, ZSM 48, ZSM 43, ZSM 35, PSH-3, zeolite p, ZSM 38, CSZ-1, ZSM 3, ZSM 20, chabasite, particularly preferably zeolite L, mordenite, ZSM 5, ZSM 11, ZSM 12, ZSM 23 and offretite. Very particular preference is given to the zeolite types mordenite, L, ZSM 5 and ZSM 11.

Zeolites which can be used according to the invention have pore sizes of at least 5 Å, for example those in the range from 5–9 Å, preferably in the range from 5–7 Å.

As exchangeable cations the zeolites can contain, for example, those of Li, Na, K, Mg, Cu, Ca, Zn, rare earth metals, Ti, Zr, Sn(IV), Cr(III), Fe(II), Mn(II), Co, Ni and others. According to the invention, those zeolites are preferred in which at least a portion of the metal ions have been exchanged for hydrogen ions, preferably 50 to 100%, particularly preferably 80 to 100% of all metal cations initially present. The acidic H+ forms of zeolites are preferably formed by exchanging the metal for ammonium ions followed by calcination. A further possibility for zeolites having an n/m value of 5 or greater consists in carrying out the proton exchange with mineral acids. Accordingly, further preferred for the process according to the invention the H forms of the zeolites -of the structure type mordenite, ZSM 5, ZSM ii, zeolite L, ZSM i2, ZSM 23 and offretite are used.

The zeolite catalyst can be used in an amount of 1-100% by weight, preferably 5-50% by weight, particularly preferably 10 to 30% by weight, relative to the total weight of the organic reactants to be reacted.

The zeolite catalyst can be reused several times in the process according to the invention. If losses in activity should occur after reusing it several times, it can be regenerated in a manner known to one skilled in the art, for example by washing, acid treatment and calcination.

The acylation reaction can in general be carried out in the melt, if permitted by the melting and boiling point conditions of the reactants. However, it is of course also possible to use solvents. Suitable solvents are those which are inert with respect to the zeolites used and the acylating agents under the reaction conditions, for example hydrocarbons or halohydrocarbons such as petroleum ether, cyclohexane or dichlorobenzene, ethers such as tetrahydrofuran or dioxane. This list is by no means exhaustive.

The process according to the invention can be carried out continuously or batchwise, at atmospheric, reduced or superatmospheric pressure. Furthermore, the acylation according to the invention can be carried out in the gas phase or in the liquid phase. For the reaction in the gas phase, the zeolite catalyst is installed in a reaction tube in compact form. For the liquid phase, the zeolite catalyst is usually used in powdered form. The preferred embodiment is that in the liquid phase; it can be carried out in a liquid-phase, trickle-bed or slurry reactor. The abovementioned use of pressure, which is not critical as such, is used for the preferred procedure in the liquid phase merely to maintain low-boiling reactants in this preferred liquid phase.

The process according to the invention is carried out at a temperature of 25°–400° C.. For the gas phase, the higher temperature range, for example 140°–400° C., is used, for the liquid phase, the lower temperature range, for example 25°–250° C., preferably 120° to 200° C., is used.

Isolation and purification of the acylated final products is carried out after the reaction is completed by known conventional techniques, for example, after the catalyst has been separated off, by distillation and/or recrystallization and/or chromatographic methods.

Unconsumed starting materials as well as the recovered catalyst can be recycled into the process according to the invention.

The pressure for the liquid phase can be the resulting internal pressure in an autoclave; however, it can also be reinforced by an additive inert gas pressure of, for example, additional 0.01–50 bar. Examples of inert gases are $N_2$, He, Ar or $CO_2$.

EXAMPLES

In the examples, the following zeolites were used:

| Example | Type | $SiO_2/Al_2O_3$ |
| --- | --- | --- |
| 1 | H-Mordenite | 25 |
| 2 | H-ZSM 5 | 110 |
| 3 | H-Zeolite L | 6 |
| 4 | H-Zeolite L | 7.5 |
| 5 | H-Mordenite | 25 |
| 6 | H-Mordenite | 16 |
| 7 | H-ZSM 11 | 65 |
| 8 | H-Offretite/Enionite | 6 |
| 9 | H-ZSM 5 | 110 |
| 10 | H-ZSM 5 | 110 |
| 11 | H-ZSM 5 | 110 |
| 12 | H-ZSM 5 | 110 |
| 13 | H-ZSM 5 | 110 |
| 14 | H-Mordenite | 16 |
| 15 | M-Mordenite | 16 |
| Comparison | without catalyst | |

EXAMPLE 1

216.3 g (2 mol) of anisole, 102.1 g (1 mol) of acetic anhydride and 40 g of zeolite powder were heated in a 1 l autoclave lined with a Teflon skin to 160° C. with stirring and at a nitrogen pressure of 20 bar and maintained at this temperature for 3 hours. After cooling, the composition was determined by gas chromatography. The result is shown in Table 1.

EXAMPLE 2 to 8

A mixture of 54 g (0.5 mol) of anisole, 25.5 g (0.25 mol) of acetic anhydride and 8 g of activated zeolite powder was heated to reflux (140°) and at certain intervals, samples were removed for testing by gas chromatography. The results can be seen from Table 1.

COMPARATIVE EXAMPLE

Example 2 was repeated without a catalyst; the results can also be seen from Table 1.

EXAMPLE 9

Using the same procedure as in Example 2, 37.9 g (0.35 mol) of anisole were reacted with 35.7 g (0.35 mol) of acetic anhydride in the presence of 8 g of zeolite powder. Results in Table 1.

EXAMPLE 10

Analogously to Example 2, 32.5 g (0.3 mol) of anisole were reacted with 45.9 g (0.45 mol) of acetic anhydride in the presence of 8 g of zeolite powder. Results in Table 1.

EXAMPLE 11

At a reflux temperature of 140° C., 39.3 g (0.5 mol) of acetyl chloride were added dropwise over a period of 2 hours to a suspension of 20 g of zeolite powder in 108 g (1 mol) of anisole, in the course of which the temperature dropped occasionally to 80° C.. Stirring was continued for another 8 hours at the reflux temperature, and the composition was determined by gas chromatography. The results are shown in Table 2.

EXAMPLE 12

A mixture of 54.0 g (0.5 mol) of anisole, 19.8 g (0.25 mol) of acetyl chloride and 15 g of zeolite powder were heated to reflux with stirring, during which the temperature rose to 90° C. over a period of 10 hours. The result of the analysis by gas chromatography can be seen from Table 2.

EXAMPLE 13

Analogously to Example 11, 54 g (0.5 mol) of anisole, 39.5 g (0.5 mol) of acetyl chloride and 15 g of zeolite powder were reacted with one another. The result of the determination by gas chromatography is shown in Table 2.

EXAMPLE 14

Analogously to the procedure of Example 2, 27 g (0.25 mol) of anisole, 16.25 g (0.125 mol) of propionic anhydride and 2.95 g of zeolite powder were reacted with one another at the reflux temperature of 150° C.. The findings by gas chromatography are listed in Table 3.

EXAMPLE 15

Using the same procedure as in Example 12, 27 g (0.25 mol) of anisole, 11.6 g (0.125 mol) of propionyl chloride and 3 g of zeolite powder were reacted with one another, during which the reflux temperature rose from 105° to 157° C. over a period of 5 hours. The result of the analysis by gas chromatography can be seen from Table 3.

TABLE 1

Acylation of anisole with acetic anhydride (Ac₂O)
(composition of the product in % by weight)
2-MAP = 2-methoxyacetophenone; 4-MAP = 4-methoxyacetophenone; C = conversion; S = selectivity with respect to 4-MAP.

| Ex. | Reaction time (h) | Ac₂O | Anisole | C (%) | 2-MAP | 4-MAP | S |
|---|---|---|---|---|---|---|---|
| 1 | 3 | 1.3 | 41.7 | 79.5 | 0.40 | 36.5 | 98.0 |
| 2 | 7.5 | 6.4 | 47.9 | 63.5 | — | 28.9 | 96.5 |
|   | 12.5 | 1.3 | 47.5 | 65.0 | — | 30.8 | 94.6 |
| 3 | 1 | 14.1 | 58.0 | 35.5 | 0.92 | 18.2 | 95.2 |
|   | 3 | 8.3 | 53.0 | 51.0 | 1.47 | 24.8 | 94.5 |
|   | 6 | 5.4 | 50.7 | 57.5 | 1.75 | 28.0 | 94.1 |
| 4 | 1.25 | 13.7* | 60.4 | 30.5 | — | 16.3 | 100 |
|   | 3.25 | 10.5 | 58.7 | 36.0 | — | 19.2 | 100 |
|   | 5.75 | 8.3 | 57.4 | 40.0 | 0.18 | 20.9 | 99.2 |
| 5 | 1 | 6.4 | 51.3 | 57.8 | — | 28.9 | 100 |
|   | 3 | 3.2 | 47.1 | 70.5 | — | 34.9 | 100 |
|   | 5 | 2.6 | 45.4 | 76.0 | — | 37.1 | 100 |
| 6 | 1 | 9.3 | 55.6 | 45.0 | — | 22.9 | 100 |
|   | 3 | 8.3 | 54.4 | 48.5 | — | 24.7 | 100 |
|   | 5.5 | 5.8 | 54.3 | 50.0 | — | 25.5 | 100 |
| 7 | 0.75 | 16.6 | 61.3 | 27.0 | — | 14.5 | 100 |
|   | 2.75 | 10.2 | 56.4 | 43.0 | — | 21.8 | 100 |
|   | 6.75 | 6.1 | 54.8 | 48.8 | — | 24.7 | 99.3 |
| 8 | 1 | 14.4 | 65.0 | 16.5 | — | 10.7 | 100 |
|   | 3 | 15.7 | 63.5 | 21.5 | — | 12.1 | 100 |
|   | 5.5 | 14.1 | 63.4 | 22.5 | — | 12.7 | 100 |
|   | Comp.1-8 | 32.07 | 67.9 | 0 | — | — | 0 |
| 9 | 1 | 18.6 | 27.4 | 48.0 | — | 32.5 | 99.6 |
|   | 10 | 17.7 | 24.3 | 53.5 | — | 37.3 | 95.7 |
| 10 | 1.75 | 40.9 | 16.2 | 61.5 | — | 35.2 | 99.3 |
|   | 4.25 | 37.1 | 14.6 | 66.0 | — | 37.7 | 99.0 |
|   | 6.5 | 27.9 | 14.2 | 66.5 | — | 40.8 | 100 |

TABLE 2

Acylation of anisole with acetyl chloride in a molar ratio of anisole:acetyl chloride = 2:1 (Examples 11 and 12) or 1:1 (Example 13). Further details as in Table 1.

| Ex. | Reaction time (h) | −temp. (°C.) | Anisole | 2-MAP | 4-MAP | S |
|---|---|---|---|---|---|---|
| 11 | 4 | 140 down | 57.3 | — | 22.5 | 96.8 |
|   | 10 | to 80 | 60.6 | — | 22.4 | 96.8 |
| 12 | 1.5 | 35 | 72.5 | 0.46 | 2.4 | 72.2 |
|   | 6 | up to | 75.6 | 0.30 | 2.2 | 73.9 |
|   | 9.75 | 90 | 64.7 | 0.83 | 14.3 | 90.6 |
| 13 | 1 | 140 down | 62.2 | 1.2 | 13.3 | 91.7 |
|   | 6 | to 80 | 61.2 | 1.2 | 14.1 | 92.2 |

TABLE 3

Acylation of anisole with C₂H₅CO-X in a molar ratio of 2:1 (X = OCO—C₂H₅ in Example 14; X = Cl in Example 15). 2-MPP and 4-MPP = 2- and 4-methoxypropylphenone. Further details as in Table 1 or 2.

| Ex. | Reaction time (h) | −temp. (°C.) | Anisole | C₂H₅-COX | 2-MPP | 4-MPP | S |
|---|---|---|---|---|---|---|---|
| 14 | 2 | 150 | 38.1 | 5.1 | 0.55 | 37.5 | 98.6 |
|   | 4 | 150 | 33.7 | 0.6 | 0.64 | 43.0 | 98.5 |
|   | 6 | 150 | 33.3 | 0.2 | 0.74 | 42.6 | 98.3 |
| (Starting mixture |   |   | 62.4 |   | 37.6) |   |   |
| 15 | 1 | 150-157 | 58.1 | 1.4 | 0.28 | 22.9 | 98.8 |
|   | 2 | 150-157 | 53.4 | 1.4 | 0.37 | 28.2 | 98.7 |
|   | 3 | 150-157 | 46.7 | 1.1 | 0.37 | 34.0 | 98.9 |
|   | 4 | 150-157 | 42.6 | 0.5 | 0.46 | 40.4 | 98.9 |

What is claimed is:

1. A process for the preparation of phenylketones etherified in the 4-position of the formula

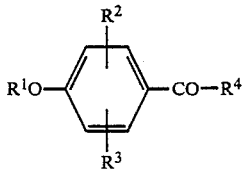

by reaction or aromatic ethers of the formula

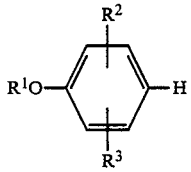

with acylating agents of the formula $$X\text{—}CO\text{—}R^4$$

in which formulae
R¹ stands for C₁–C₁₂-alkyl, C₂–C₁₂-alkenyl, C₃–C₇-cycloalkyl or C₆–C₁₀-aryl,
R² and R³ independently of one another denote hydrogen, fluorine, chlorine, bromine, C₁–C₄-alkyl or C₃–C₇-cycloalkyl,
R⁴ denotes C₁–C₁₆-alkyl, C₂–C₁₆-alkenyl, C₃–C₇-cycloalkyl, C₇–C₁₂-aralkyl, C₈–C₁₂-aralkenyl or C₆–C₁₂-aryl and
X stands for chlorine, bromine, OCOR⁴, C₁–C₄-alkoxy, hydroxyl, amino, NH—C₁–C₄-alkyl or N(C₁–C₄-alkyl)₂ wherein the reactants to be reacted are present in the liquid phase and the acylation reaction is carried out in the presence of zeolite catalysts of the formula

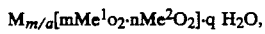

in which
- M is an exchangeable cation,
- z is the valence of the cation,
- $Me^1$ and $Me^2$ represent the elements of the anionic skeleton,
- n/m denotes the ratio of the elements and adopts values of 1-3000, and
- q denotes the amount of the water absorbed; the zeolites having pore sizes of at least 5 Å and the zeolites used are those of the structures faujasite, L, mordenite, mazzite, offretite, gmelinite, cancrinite, ZSM 12, ZSM 25, zeolite β, ferrierite, ZSM 5, ZSM 11, heulandite, ZSM 22, ZSM 23, ZSM 48, ZSM 43, ZSM 35, PSH-3, zeolite ρ, ZSM 38, CSZ-1, ZSM 3, ZSM 20, chabasite.

2. The process of claim 1, wherein the ratio of the elements n/m adopts values of 1-2000.

3. The process of claim 1 wherein the zeolites have a pore size of 5-9 Å.

4. The process of claim 3, wherein the zeolites have a pore size of 5-7 Å.

5. The process of claim 1, wherein 0.2-5 mole of ether are used per mole of acylatinq agent.

6. The process of claim 5, wherein 0.5-2 mole of ether are used per mole of acylatinq agent.

7. The process of claim 1, wherein the acylating agents used are the anhydrides or the acid chlorides.

8. The process of claim 1, wherein the reaction is carried out in the presence of 1-100% by weight of zeolite catalysts, relative to the total weight of the organic reactants to be reacted.

9. The process of claim 8, wherein the reaction is carried out in the presence of 5-50% by weight of zeolite catalysts, relative to the total weight of the organic reactants to be reacted.

10. The process of claim 9, wherein the reaction is carried out in the presence of 10-30% by weight of zeolite catalysts, relative to the total weight of the organic reactants to be reacted.

11. The process of to claim 1, wherein $Me^1$ is a trivalent element.

12. The process of claim 11, wherein the trivalent element is aluminum.

13. The process of claim 1, wherein the zeolites used are of the structures of L, mordenite, ZSM 5, ZSM 11, ZSM 12, ZSM 23 or offretite.

14. The process of claim 13, wherein the zeolites used are of the structures of mordenite, L, ZSM 5 or ZSM 11.

15. The process of claim 1, wherein 50 to 100% of the exchangeable cations are $H^+$ ions.

16. The process of claim 15, wherein 80-100% of the exchangeable cations are $H^+$ ions.

17. The process of claim 15, wherein the $H^+$ forms of mordenite, ZSM 5, ZSM 11, L, ZSM 12, ZSM 23 and offretite are used.

18. The process of claim 1, wherein the acylating agent is used in a stoichiometric ratio with respect to the aromatic ether.

UNITED STATES PATENT AND TRADEMARK OFFICE
CERTIFICATE OF CORRECTION

PATENT NO. : 4,960,943

DATED : October 2, 1990

INVENTOR(S) : Botta et al.

It is certified that error appears in the above-identified patent and that said Letters Patent is hereby corrected as shown below:

Title Page      [30] Foreign Application Priority Data: Insert -- Jun. 14, 1988 [DE] Fed. Rep. of Germany ... 3820193 --

Col. 9, line 1    After " wherein the " insert -- organic --

Col. 9, line 5    After " $M_m/$ " delete " a " and substitute -- $z$ --

Signed and Sealed this

Fourteenth Day of July, 1992

Attest:

DOUGLAS B. COMER

Attesting Officer     Acting Commissioner of Patents and Trademarks